United States Patent [19]

Dannenberg et al.

[11] 4,302,614
[45] Nov. 24, 1981

[54] 2,2-BIS[4-(2,3-DIBROMOPROPOXY)-3,5-DIBROMOPHENYL]-PROPANE PROCESS

[75] Inventors: Wolfgang Dannenberg, Wunstorf; Walter Heyer, Barsinghausen; Theo Döldissen, Seelze; Manfred Zimmermann, Hanover, all of Fed. Rep. of Germany

[73] Assignee: Riedel-de Haen Aktiengesellschaft, Hanover, Fed. Rep. of Germany

[21] Appl. No.: 120,331

[22] Filed: Feb. 11, 1980

[30] Foreign Application Priority Data

Feb. 13, 1979 [DE] Fed. Rep. of Germany ....... 2905397

[51] Int. Cl.³ .............................................. C07C 41/01
[52] U.S. Cl. .................................................. 568/641
[58] Field of Search ......................................... 568/641

[56] References Cited

U.S. PATENT DOCUMENTS 3,895,077 7/1975 Brady et al. ..................... 568/641

FOREIGN PATENT DOCUMENTS 49-20155 2/1974 Japan ................................. 568/641

49-125348 11/1974 Japan ................................. 568/641

Primary Examiner—Bernard Helfin
Attorney, Agent, or Firm—Curtis, Morris & Safford

[57] ABSTRACT 2,2-Bis[4-(2,3-dibromopropoxy)-3,5-dibromophenyl]-propane (BDDP) has the structural formula

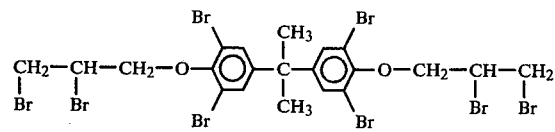

This bisphenol-A derivative is prepared by reaction of 2,2-bis[4-hydroxy-3,5-dibromophenyl]-propane with an allyl halide and subsequent bromination of the diallyl ether obtained. In the first reaction step, a lower aliphatic alcohol is used as solvent, and in the second reaction step an aromatic halogenated hydrocarbon. The reaction product is then precipitated by excess alcohol, and separated. The BDDP is obtained in the form of granules and is suitable for application as flameproofing agent.

12 Claims, No Drawings

2,2-BIS[4-(2,3-DIBROMOPROPOXY)-3,5-DIBROMOPHENYL]-PROPANE PROCESS

The invention provides 2,2-bis[4-(2,3-dibromopropoxy)-3,5-dibromophenyl]-propane and a process for the manufacture thereof by reaction of 2,2-bis-[4-hydroxy-3,5-dibromophenyl]-propane with an allyl halide, and bromination of the diallyl ether so obtained with bromine.

2,2-Bis[4-(2,3-dibromopropoxy)-3,5-dibromophenyl]-propane (hereinafter called BDDP) is a derivative of tetrabromo-bisphenol A, and described in German Offenlegungsschrift No. 22 10 916 (=U.S. Pat. No. 3.904.694). It is used as flameproofing agent in the plastics industry, often in combination with antimony trioxide, and it has the following formula:

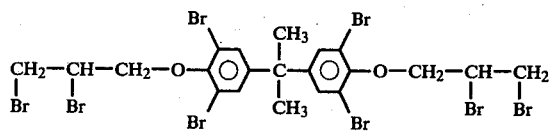

Several processes for the manufacture of BDDP have been proposed: For example, according to German Offenlegungsschrift No. 22 26 694 (=British Pat. No. 13 34 638) and German Auslegeschrift No. 25 52 713, tetrabromo-bisphenol A (2,2-bis[4-hydroxy-3,5-dibromophenyl]-propane (hereinafter called BHDP) is etherified in an alkaline alcohol solution, and the reaction product, that is, the BHDP diallyl ether, is isolated. Subsequently, the compound so obtained is brominated in chloroform or carbon tetrachloride, and the solvent is removed by distillation. The product obtained is a highly viscous yellowish liquid which hardens after prolonged standing. According to German Offenlegungsschrift No. 22 10 916, bromination and subsequent precipitation of the isolated BHDP diallyl ether is carried out in a monocarboxylic acid such as acetic acid. The product is obtained in suspended form, and is separated and worked up in known manner. According to Japanese Patent Publication No. 74 125 348, it is first brominated in methylene chloride, and after having distilled off the solvent, it is absorbed in an aliphatic ketone for crystallization, in order to attain a higher melting range.

According to the known processes it is in any case necessary to isolate the BHDP diallyl ether in the form of a crystalline intermediate product in order to avoid quality losses in the subsequent bromination. In such separation operations, great expenditure and reduced yields are always to be expected. The products obtained are of greatly varying quality; there may result highly viscous or solidified liquids having a low melting range, or finely crystalline to pulverulent powders which in the further processing tend to agglomerate when being mixed. Moreover, the use of chloroform as solvent requires increased safety precautions because of the toxicity known to those skilled in the art. Due to its solubility properties and the very difficult drying, acetic acid is no ideal bromination agent, either. Although the use of aliphatic ketones as a crystallization agent results in higher melting ranges, the final product is of an increased solubility degree which results in reduced yields.

It is therefore the object of the present invention to provide a process for the manufacture of BDDP which simplifies the operations, brings about an increase of yield and results in a product form capable of being further processed without any difficulty.

Accordingly, the present invention provides 2,2-bis[4-(2,3-dibromopropoxy)-3,5-dibromophenyl]-propane, obtainable by (a) reaction of 2,2-bis [4-hydroxy-3,5-dibromophenyl]-propane with an allyl halide in solution in a mixture of water and a lower aliphatic alcohol, (b) removal of the lower aliphatic alcohol, (c) dissolution of the allyl ether obtained according to (b) in an aromatic halogenated hydrocarbon and removal of the water, (d) bromination of the allyl ether with bromine, (e) removal of excess bromine, (f) washing of the bromoallyl ether solution obtained according to (e) with water, (g) precipitation of the bromoallyl ether by means of a lower aliphatic alcohol, and subsequent separation.

The invention provides furthermore a process for the manufacture of 2,2-bis[4-(2,3-dibromopropoxy)-3,5-dibromophenyl]-propane by reaction of 2,2-bis[4-hydroxy-3,5-dibromophenyl]-propane with an allyl halide in an alcoholic solution and bromination of the allyl ether obtained with bromine, which comprises (a) reacting 2,2-bis[4-hydroxy-3,5-dibromophenyl]-propane with the allyl halide in solution in a mixture of water and a lower aliphatic alcohol, (b) removing the lower aliphatic alcohol, (c) dissolving the allyl ether obtained according to (b) in an aromatic halogenated hydrocarbon and removing the water, (d) brominating the allyl ether with bromine, (e) removing the excess bromine, (f) washing the bromallyl ether solution obtained according to (e) with water, (g) precipitating the bromoallyl ether by means of a lower aliphatic alcohol, and subsequently separating it.

The starting material BHDP can be prepared according to known processes, for example by brominating 2,2-bis[4-hydroxyphenyl]-propane (=bisphenol A) with 4 to 4.5 mols of elementary bromine per mol of bisphenol at a temperature of from 15° to 45° C. in an aliphatic, preferably aqueous, alcohol having from 1 to 4 carbon atoms (see German Pat. No. 1 268 149=U.S. Pat. No. 3.029.291). In this process, a mixture of methanol and water in a weight ratio of from 1:1 to 3:1 is preferably used. In order to complete the reaction, the reaction mixture may be finally heated for a certain time at the boiling temperature of the alcohol/water mixture.

The BHDP is reacted in an aqueous alcoholic solution with an allyl halide, for example allyl bromide or, preferably, allyl chloride, to form the corresponding allyl ether. As alcohol, a lower aliphatic alcohol having preferably 1, 2 or 3 carbon atoms is used, for example methanol, ethanol, n-propanol or isopropanol; methanol being preferably employed. The weight ratio of water to alcohol is from 30:70 to 70:30, preferably 45:55 to 55:45. Allylation is carried out at a temperature of from 35° to 45° C., preferably 38° to 42° C., in an alkaline medium. The pH of this medium is in the range of from 11.5 to 13.0, preferably 11.8 to 12.2, and it is adjusted by means of an inorganic base, preferably an alkali metal hydroxide such as especially sodium hydroxide or potassium hydroxide. The reaction is complete when heavy precipitation and alteration of the pH towards 7 is observed.

Subsequently, the alcohol is removed from the reaction mixture, preferably by distillation, optionally under reduced pressure. An aromatic halogenated hydrocarbon is added to the aqueous suspension in an amount sufficient for dissolving the precipitated allyl ether, especially in an amount of from 0.5 to 2 liters, preferably 1.2 to 1.6 liters (relative to 1 mol of BHDP). The allyl ether is dissolved in the halogenated hydrocarbon, thus forming two well separable phases.

Suitable aromatic halogenated hydrocarbons are mono-, di- or trihalogenated aromatic hydrocarbons having preferably 6 or 7 carbon atoms, for example chlorobenzene, bromobenzene, fluorobenzene, 2-chlorotoluene, 2-bromotoluene, 2-fluorotoluene, 1,2-dichlorobenzene or benzotrichloride. Instead of one single halogenated hydrocarbon, a mixture of two or more of them may alternatively be employed.

The solution of the allyl ether in the aromatic halogenated hydrocarbon is used for bromination without any further work-up; isolation of the allyl ether is therefore unnecessary. Surprisingly, this simplification of the process adversely affects neither the quality of the product nor the yield.

The allyl ether dissolved in the aromatic halogenated hydrocarbon is brominated with elementary bromine in an amount of from 2.0 to 2.4 mols, preferably 2.2 to 2.3 mols, per mol of allyl ether, generally at a temperature of from 10° to 30° C., preferably 15° to 25° C.

After bromination, excess bromine is removed, preferably by means of sodium bisulfite. Subsequently, the bromoallyl ether (BDDP) solution is washed with water, preferably several times, at a temperature of from 30° to 50° C., preferably 35° to 45° C.

The 2,2-bis[4-(2,3-dibromopropoxy)-3,5-dibromophenyl]-propane is precipitated from the solution so purified by mixing with a lower aliphatic alcohol. Suitable are the abovementioned alcohols, preferably methanol, used generally in excess. Precipitation is carried out at a temperature of from 10° to 30° C., preferably 15° to 25° C. Addition of seed crystals is advantageous, and it is furthermore recommended to keep the mixture in constant motion, preferably by agitation. It is especially advantageous to precipitate the BDDP by introducing the BDDP solution in the aromatic hydrocarbon into the 1- to 4-fold volume of the lower aliphatic alcohol. The precipitated BDDP is then separated, preferably by suction-filtration of the liquid components of the precipitation mixture, and dried at a temperature of from 35° to 70° C.

The BDDP in accordance with the invention is obtained in the form of purely white granules having an average particle diameter of from preferably 500 to 1000 μm. The melting range is from 95° to 110° C., and the average apparent density from 0.7 to 1.0 g/cm$^3$. The granules do not tend to agglomeration or deposit formation on further processing; moreover, they have an excellent flow.

The following examples illustrate the invention; percentages being by weight.

EXAMPLE 1

1,000 liters of drinking water are introduced into a 5 m$^3$ vessel of rubber-coated steel with distilling column, and 179 kg of sodium hydroxide (4.48 kmols) are dissolved therein with agitation. 1,260 l of methanol and 1,100 kg of BHDP (tetrabromobisphenol A) (2 kmols) are added one after the other. A light brown, clear solution is formed having a pH of about 12. After heating to 40° C., 376 kg of allyl chloride (4.88 kmols) are added in several portions within one hour to the clear solution, while the temperature is maintained at 40° C. The addition of allyl chloride being complete, the reaction mixture is maintained at boiling temperature for 5 hours. The bottom temperature thus rises from about 44° C. to about 47° C. Heavy precipitation occurs. The pH is about 7 towards the end of the reaction.

About 1,000 l of methanol are distilled off from the reaction mixture. After cooling to about 60° C. at the bottom, 1,500 l (1,650 kg) of chlorobenzene are introduced into the residue with constant agitation, which causes dissolution of the precipitate and formation of two well separable phases. The aqueous upper phase of the mixture is thoroughly separated. Subsequently, the chlorobenzene phase is brominated; 728 kg of bromine (4.55 kmols) are metered into the clear solution with agitation at about 20° C. and slight cooling. Subsequently, agitation is continued for 1 hour. For reduction of the excess bromine amount, 1,500 l of water and 50 kg of sodium bisulfite are added, and the batch is agitated. When the reaction mixture is of a light yellow color, it is again washed 3 times with 500 l each of water. The pH is then adjusted to 6 to 6.5 by means of soda, and the last washing water is completely ladled out. The temperature of the reaction mixture is maintained at 40° C. during the whole washing operation.

In order to precipitate the batch, 4,800 l of methanol (=3,800 kg) are introduced into another vessel of rubber-coated steel having a capacity of 10 m$^3$, and 25 kg of seed crystals are added. At a temperature of about 20° C. the chlorobenzene solution is poured in, first slowly and then rapidly towards the end of the precipitation. Grainy, purely white granules are obtained as precipitate, which are suction-filtered immediately after precipitation is complete, washed with methanol and dried.

The mother liquid may be subjected to fractional distillation and the methanol and chlorobenzene fractions obtained can be directly reused.

After drying of the suction-filtered product at 60° C. in a drying cabinet with air circulation, the yield is 1,800 kg of BDDP (94.3% of theory, relative to BHDP).

The product is obtained in the form of grainy, purely white granules having an average particle diameter of about 500 μm, a bromine content of 65 to 67%, a melting range of 100° to 110° C. and an apparent density of about 0.7 g/cm$^3$. When the substance is heated to a temperature of above 200° C., the melt becomes slightly yellow.

EXAMPLE 2

44.7 g of sodium hydroxide (1.12 mols) and 275 g of BHDP (tetrabromobisphenol A) (0.5 mol) are introduced one after the other into a solvent mixture of 250 ml of drinking water and 315 ml of methanol. After some time, a light brown, clear solution forms which has a pH of about 12. After heating to 40° C., 94 g of allyl chloride (1.22 mols) are added dropwise, while maintaining the temperature at 40° C. The addition of allyl chloride being complete, the reaction mixture is refluxed for 5 hours. Heavy precipitation occurs; towards the end of the reaction the pH is about 7. About 250 ml of methanol are distilled off from the reaction mixture. After cooling to a bottom temperature of about 60° C., 375 ml of bromobenzene (=562 g) are added with constant agitation to the residue, which causes dissolution of the precipitate and formation of two well separable phases. The upper aqueous phase is removed from the mixture and rejected. The bromobenzene phase is subsequently brominated with agitation and slight exterior cooling at a temperature of about 20° C., by adding dropwise 182 g of bromine (1.14 mols). Agitation is continued for 1 hour. For reduction of the excess bromine amount, 250 ml of drinking water and 12 g of sodium bisulfite are added, and the batch is agitated. When the bromine color has disappeared and the aqueous phase is separated, the batch is washed three times with 200 ml each of water (at 40° C.), and the last washing water is thoroughly removed.

For precipitation, 1,200 ml (=950 g) of methanol and 7.5 g of seed crystals are introduced into another vessel. At a temperature of about 20° C., the bromobenzene solution is poured in first slowly and then rapidly towards the end of the precipitation. Grainy, purely white granules precipitate, which, after the precipitation is complete, are suction-filtered, washed with 200 ml of methanol and dried at 60° C. After drying, the yield is 407 g of BDDP (86% of theory, relative to BHDP). The average particle diameter is about 1,000 μm, the bromine content 65 to 67%, the melting range 95.5° to 100° C., and the apparent density about 0.7 g/cm$^3$.

EXAMPLE 3

Example 2 is repeated with the use of 500 ml of fluorobenzene. The same yield is obtained. The product obtained corresponds to that of Example 2, but has an average grain size of 500 to 800 μm.

In analogous manner, the above process can be carried out with the use of benzotrichloride, chlorotoluene, fluorotoluene, or dichlorobenzene as halogenated aromatic hydrocarbons.

What is claimed is:

1. A process for the manufacture of 2,2-bis[4-(2,3-dibromopropoxy)-3,5-dibromophenyl]-propane by reaction of 2,2-bis[4-hydroxy-3,5-dibromophenyl]-propane with an allyl halide in an alcoholic solution and bromination of the allyl ether obtained with bromine, which comprises (a) reacting 2,2-bis[4-hydroxy-3,5-dibromophenyl]-propane with the allyl halide in solution in a mixture of water and a lower aliphatic alcohol, (b) removing the lower aliphatic alcohol, (c) dissolving the allyl ether obtained according to (b) in an aromatic halogenated hydrocarbon and removing the water, without further workup of the allyl ether after it is dissolved in the aromatic halogenated hydrocarbon in step (c), (d) brominating the allyl ether with bromine (e) removing the excess bromine, (f) washing the thus obtained brominated allyl ether solution obtained according to (e) with water, (g) precipitating the brominated allyl ether by means of a lower aliphatic alcohol, and subsequently separating it.

2. The process as claimed in claim 1, which comprises using as lower aliphatic alcohol an alkanol having 1, 2 or 3 carbon atoms.

3. The process as claimed in claim 1, which comprises using as aromatic halogenated hydrocarbon a mono-, di- or trihalogenated aromatic hydrocarbon having 6 or 7 carbon atoms.

4. The process as claimed in claim 1, which comprises using the aromatic halogenated hydrocarbon in an amount of from 0.5 to 2 liters per mol of allyl ether.

5. The process as claimed in claim 1, which comprises precipitating the bromoallyl ether by introducing the solution of the bromoallyl ether in the aromatic halogenated hydrocarbon into the 1- to 4-fold volume of the lower alcohol.

6. The process as claimed in claim 1, wherein the ratio of water to alcohol is in a range of from 30:70 to 70:30 parts by weight.

7. The process as claimed in claim 6, wherein the water to alcohol ratio is in a range of from 45:55 to 55:45 parts by weight.

8. The process as claimed in claim 1, wherein the reaction of 2,2-bis[4-hydroxy-3,5-dibromophenyl]-propane with the allyl halide is carried out at a temperature of from 35° to 45° C. in an alkaline medium having a pH in the range of 11.5 to 13.0.

9. The process as claimed in claim 3, wherein the aromatic halogenated hydrocarbon is chlorobenzene, bromobenzene, fluorobenzene, 2-chlorotoluene, 2-bromotoluene, 2-fluorotoluene, 1,2-dichlorobenzene or benzotrichloride.

10. The process as claimed in claim 1, wherein the allyl ether dissolved in the aromatic halogenated hydrocarbon is brominated with elemental bromine in an amount of from 2.0 to 2.4 moles per mole of allyl ether.

11. The process as claimed in claim 1, wherein the lower aliphatic alcohol used to precipitate the brominated allyl ether is methanol.

12. The process as claimed in claim 1, including in step (g) precipitating the bromoallyl ether by means of a lower aliphatic alcohol, and subsequently separating the brominated allyl ether to yield granules having an average particle diameter of 500 to 1000 μm., a melting range of from 95° to 110° C. and an average apparent density of from 0.7 to 1.0 g/cm$^3$.

* * * * *